United States Patent
Kim

(10) Patent No.: US 11,672,753 B2
(45) Date of Patent: Jun. 13, 2023

(54) COMPOSITION FOR SEBUM CONTROL AND PORE MINIMIZING

(71) Applicant: AMOREPACIFIC CORPORATION, Seoul (KR)

(72) Inventor: Jeong Hwan Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 132 days.

(21) Appl. No.: 16/767,446

(22) PCT Filed: Sep. 21, 2018

(86) PCT No.: PCT/KR2018/011291
§ 371 (c)(1),
(2) Date: May 27, 2020

(87) PCT Pub. No.: WO2019/107723
PCT Pub. Date: Jun. 6, 2019

(65) Prior Publication Data
US 2021/0369594 A1 Dec. 2, 2021

(30) Foreign Application Priority Data

Nov. 28, 2017 (KR) .................... 10-2017-0160504
Sep. 20, 2018 (KR) .................... 10-2018-0113116

(51) Int. Cl.
*A61K 36/00* (2006.01)
*A61K 8/9789* (2017.01)
*A61K 8/9728* (2017.01)
*A61Q 19/00* (2006.01)

(52) U.S. Cl.
CPC .......... *A61K 8/9789* (2017.08); *A61K 8/9728* (2017.08); *A61Q 19/008* (2013.01)

(58) Field of Classification Search
CPC .................................................. A61Q 19/00
See application file for complete search history.

(56) References Cited

U.S. PATENT DOCUMENTS

| 2004/0101577 A1 | 5/2004 | Ahn et al. | |
| 2012/0141613 A1* | 6/2012 | Kim | A61K 36/73 424/728 |
| 2015/0306024 A1 | 10/2015 | Kim et al. | |

FOREIGN PATENT DOCUMENTS

| CN | 1218680 A | * | 6/1999 |
| CN | 102573787 | | 7/2012 |
| CN | 103784367 A | | 5/2014 |
| CN | 103948817 A | | 7/2014 |
| CN | 105560151 A | * | 5/2016 |
| CN | 105919884 A | | 9/2016 |
| CN | 106176385 A | | 12/2016 |
| CN | 106421721 A | | 2/2017 |
| CN | 107029050 A | | 8/2017 |
| JP | H10194947 A | * | 7/1998 |
| KR | 10-2002-0078709 A | | 10/2002 |
| KR | 2003-0021991 A | | 3/2003 |
| KR | 10-2005-0108720 A | | 11/2005 |
| KR | 10-0851408 B1 | | 8/2008 |
| KR | 10-2008-0094457 A | | 10/2008 |
| KR | 10-2012-0058738 A | | 6/2012 |
| KR | 10-2014-0145268 A | | 12/2014 |
| KR | 10-2014-0145278 A | | 12/2014 |
| KR | 2014145278 A | * | 12/2014 |
| KR | 10-1527228 B1 | | 6/2015 |

OTHER PUBLICATIONS

Bashar Saad et al., "Arab Herbal Medicines", Botanical medicine in clinical practice, 2008, pp. 31-39, Chapter 4.
International Search Report for PCT/KR2018/011291, dated Jan. 14, 2019.
Chinese Patent Office, Communication dated Jun. 6, 2022 in Chinese Application No. 201880077196.0.
China Food and Drug Administration, "Safety and Technical Standards for Cosmetics", 2015, 7 pages.
Chinese Patent Office, Communication dated Dec. 28, 2022 in Chinese Application No. 201880077196.0.
Korean Patent Office, Communication dated Feb. 1, 2023 Korean Application No. 120060241378, with English translation.

* cited by examiner

*Primary Examiner* — Qiuwen Mi
(74) *Attorney, Agent, or Firm* — Sughrue Mion, PLLC

(57) ABSTRACT

A composition for sebum control and pore reduction, and its use for controlling sebum and reducing pore of skin are disclosed. The external-use skin preparation composition contains, as an active ingredient, extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica*, and thus it not only can control the production of sebum and alleviate skin troubles, but also provide antioxidant effects, prevent pore enlargement, or prevent occurrence of skin irritation.

3 Claims, No Drawings

COMPOSITION FOR SEBUM CONTROL AND PORE MINIMIZING

CROSS REFERENCE TO RELATED APPLICATIONS

This application is a National Stage of International Application No. PCT/KR2018/011291 filed Sep. 21, 2018, claiming priority based on Korean Patent Application No. 10-2017-0160504 filed Nov. 28, 2017 and Korean Patent Application No. 10-2018-0113116 filed Sep. 20, 2018, the entire content of which is hereby incorporated by reference.

TECHNICAL FIELD

One aspect of the present disclosure relates to a composition for sebum control and pore reduction, and more specifically to an external-use skin preparation composition containing, as an active ingredient, extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica*, and thereby, it not only can control the production of sebum and alleviate skin troubles, but also provide antioxidant effects, prevent pore enlargement, and prevent occurrence of skin irritation. One aspect of the present disclosure relates to the use of extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica*, as an active ingredient, in the preparation of a cosmetic composition, preferably a composition for sebum control and pore reduction. In addition, One aspect of the present disclosure relates to a method for controlling sebum and/or reducing pores of a subject, including locally applying a cosmetic composition containing, as an active ingredient, extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica* to the skin of the subject.

BACKGROUND ART

In the skin including the scalp and face, sebum generally functions to keep the skin moisturized or prevent the invasion of microorganisms. However, when sebum is excessively secreted, it can lead to various disorders, for example, hair loss is accelerated, acne worsens, pore enlargement is accelerated due to acne, and seborrheic dermatitis occurs.

Such excessive secretion of sebum is caused by various factors. Among them, the most important factor is that sebaceous gland cells are activated and the sebum is excessively secreted by the amount of dihydrotestosterone (DHT), which is one of the hormones involved in promotion of sebum secretion, in terms of the activity of the sebaceous glands. That is, during hair loss, testosterone is converted into DHT, a type of androgen, by 5-α-reductase type 2 in cells, and at the same time, binds to a receptor in the cytoplasm and enters the nucleus, thus causing hair loss. In contrast, in the skin or sebaceous glands, testosterone is converted into DHT by 5-α-reductase type 1 to activate sebaceous gland cells, which accelerates the differentiation of the cells, and thus serum is secreted excessively in the sebaceous glands, thereby causing acne (J. Invest Dermatol 105:209-214 Diane etc.).

In addition to the simple excessive secretion of sebum, skin troubles such as acne, hair loss or the like are further aggravated by microinflammations of the skin. In the acne formation process, excessive accumulation of sebum in hair follicles activates the acne germs (*Propionibacterium acnes*) and causes inflammation.

Meanwhile, as the aging progresses, the size of the pores widens around the T-zone region, causing cosmetic problems. The enlarged pores can be improved through hospital surgery, but there are still problems in that there are personal differences in the improvement, the degree of satisfaction is not good and the effect is temporary. In addition, although cosmetic products for pore care are available, it only gives a feeling that the pores are temporarily tightened, and the effect of improving the pores over the long term is slight.

However, there are not many raw materials which can reduce pores while reducing sebum secretion through fundamental causes, as a natural material safe for the skin.

PRIOR ART DOCUMENT

[Patent Document]
1. Korean Patent Application Publication No. 2012-0058738 (published on Jun. 8, 2012)

DETAILED DESCRIPTION OF THE INVENTION

Technical Problem

Accordingly, the present inventors have found that the extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica* are associated with sebum control, antioxidant effects, prevention of pore enlargement, pore reduction, and improvement of skin elasticity, thereby completing the present disclosure.

Therefore, it is one object of the present disclosure to provide an external-use skin preparation composition which is effective for sebum control and pore reduction.

Technical Solution

In order to achieve the above object, one aspect of the present disclosure provides an external-use skin preparation composition for sebum control and pore reduction comprising, as an active ingredient, extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica*.

Another aspect of the present disclosure provides the use of extracts of one or more medicinal herbs selected from the group consisting of *Cimicifugae rhizoma, Solani nigri herba, Glycyrrhiza uralensis, Clematis mandshurica, Acanthopanax senticosus, Inulae radix* and *Dioscorea japonica* for sebum control or pore reduction, in the preparation of a cosmetic composition.

Yet another aspect of the present disclosure provides a method for controlling sebum and/or reducing pores of a subject, comprising the step of locally applying a cosmetic composition comprising, as an active ingredient, extracts of one or more medicinal herbs selected from the group consisting of *Cimicifugae rhizoma, Solani nigri herba, Glycyr-* rhiza uralensis, Clematis mandshurica, Acanthopanax senticosus, Inulae radix and Dioscorea japonica to the skin of the subject.

Advantageous Effects

The composition of the present disclosure contains, as an active ingredient, extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica and thereby, not only provides excellent sebum control effect, but also improves skin elasticity by removing reactive oxygen species and promoting collagen synthesis, and exhibits excellent effect of reducing skin pores.

Detailed Description of the Embodiments

The composition according to the present disclosure contains extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica and thus provides excellent effect of controlling sebum or reducing skin pores.

The present disclosure provides the use of extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica, as an active ingredient, for sebum control or pore reduction, in the preparation of a cosmetic composition, preferably a composition for sebum control and pore reduction.

In addition, the present disclosure relates to a method controlling sebum and/or reducing pores of a subject, comprising the step of locally applying a cosmetic composition comprising, as an active ingredient, extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica to the skin of the subject.

As used herein, Cimicifugae rhizoma is the rhizome of Cimicifuga foetida or Cimicifuga heracleifolia, which is a perennial herbaceous plant belonging to the Ranunculaceae family. It has antibacterial, detoxifying and sedative effects and is used for the purpose of treating infectious diseases, headaches and the like.

As used herein, Solani nigri herba is the herb of Solanum nigrum, which is an annual herbaceous plant belonging to the Solanaceae family, and has anti-inflammatory, antipyretic, detoxification, blood circulation-improving and swelling-reducing effects.

As used herein, Glycyrrhiza uralensis, which is also called Licorice, is a perennial herbaceous medicinal plant belonging to the legume family and contains glycyrrhizin, flavonoids, saponins, coumarins, tannins, and enzymes in large amounts. It removes harmful oxygen produced by ultraviolet rays, prevents photooxidation of melanin, and functions to make the skin white and transparent.

As used herein, Clematis mandshurica is a plant belonging to the Ranunculaceae family, and in Chinese medicine, the root is referred to as Clematis mandshurica. It has been used as a therapeutic agent for neuralgia, muscle pain, migraine and the like, and has been reported to participate in blood pressure reduction, smooth muscle excitation, diuretic action, blood sugar reduction, pain, and antibacterial action.

As used herein, Acanthopanax senticosus is a deciduous shrub belonging to the Araliaceae family, and has been widely used for neuralgia, arthritis, hypertension, nervous breakdown and diabetes, and as tonics for a long time.

As used herein, Inulae radix is the dried root of Inula helenium L. belonging to the Asteraceae family and has the effects of promoting circulation of the spirit and energy, relieving pain, strengthening the spleen, improving the function of the stomach and allowing the liver to function well.

As used herein, Dioscorea Japonica is known to have hemostatic and antibacterial effects, be effective for dermatitis with skin cracks (various skin diseases), promote hair growth, darken hair, promote the blood flow through coronary arteries, and have sedative, analgesic, and anti-cancer effects (uterine cancer, esophageal cancer, skin cancer, and the like).

The extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica that are used in the present disclosure can be prepared by a method known in the art, and the method is not particularly limited, but preferably, a solvent and dried sample are extracted in a ratio of 10:1 using alcohol (ethanol) and heated water as an extraction solvent, followed by depressurization, filtration, and drying to prepare the extracts.

The composition according to the present disclosure may contain the extracts of one or more medicinal herbs selected from the group consisting of Cimicifugae rhizoma, Solani nigri herba, Glycyrrhiza uralensis, Clematis mandshurica, Acanthopanax senticosus, Inulae radix and Dioscorea japonica in an amount of 0.001 to 10% by weight. If the content of the extracts is less than 0.001% by weight, the efficacy and effects due to the above ingredients may be insignificant, and if it exceeds 10% by weight, there may be a problem in terms of skin safety or formulation.

The composition of the present disclosure may interfere with the expression of the 5α-reductase gene and thus inhibit or suppress its expression, or may inhibit the activity of the 5α-reductase protein, thereby preventing its action. Further, when the composition is applied to the skin, it can effectively inhibit sebum from being excessively secreted.

In addition, the composition of the present disclosure, when applied to the skin, promotes the removal of reactive oxygen species and the synthesis of collagen, thereby reducing skin pores, and has an excellent effect of suppressing skin troubles by reducing the expression of inflammatory factors. Further, it can prevent the occurrence of skin irritation due to excellent antioxidant power.

The composition of the present disclosure may be formulated as an external-use skin preparation composition, particularly as a cosmetic composition, and may be formulated by containing a cosmetically or dermatologically acceptable medium or base. In addition, the composition of the present disclosure may be provided in any form suitable for topical application, for example, in the form of solutions, emulsions obtained by dispersing oil phase in aqueous phase, emulsions obtained by dispersing aqueous phase in oil phase, suspensions, solids, gels, powders, pastes, foams or aerosols. Specifically, the composition of the present disclosure may be provided in the form of creams, skins, lotions, powders, ointments, sprays or conceal sticks. The compositions in such forms may be prepared according to a conventional method in the art.

Hereinafter, the present disclosure will be described in further detail by way of Examples. However, it will be apparent to those skilled in the art that these Examples are given for illustrative purposes only, and the scope of the disclosure is not intended to be limited to or by these Examples.

[Reference Example 1] Preparation of *Cimicifugae* Rhizome Extract

The preparation method of the *Cimicifugae rhizoma* extract of the present disclosure is as follows: 1000 ml of anhydrous ethanol was added to *Cimicifugae rhizoma* natural product (100 g) purchased from the Korea Plant Extract Bank (Daejeon, Korea), and the *Cimicifugae rhizoma* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Cimicifugae rhizoma*.

[Reference Example 2] Preparation of *Solani nigri herba* Extract

The preparation method of the *Solani nigri herba* extract of the present disclosure is as follows: 1000 ml of anhydrous ethanol was added to *Solani nigri herba* natural product (100 g) purchased from the Korea Plant Extract Bank (Daejeon, Korea), and the *Solani nigri herba* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Solani nigri herba*.

[Reference Example 3] Preparation of *Glycyrrhiza uralensis* Extract

The preparation method of the *Glycyrrhiza uralensis* extract of the present disclosure is as follows: 1000 ml of anhydrous ethanol was added to *Glycyrrhiza uralensis* natural product (100 g) purchased from the Korea Plant Extract Bank (Daejeon, Korea), and the *Glycyrrhiza uralensis* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Glycyrrhiza uralensis*.

[Reference Example 4] Preparation of *Clematis mandshurica* Extract

The preparation method of the *Clematis mandshurica* extract of the present disclosure is as follows: 1000 ml of anhydrous ethanol was added to *Clematis mandshurica* natural product (100 g) purchased from the Korea Plant Extract Bank (Daejeon, Korea), and the *Clematis mandshurica* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Clematis mandshurica*.

[Reference Example 5] Preparation of *Acanthopanax senticosus* Extract

The preparation method of the *Acanthopanax senticosus* extract of the present disclosure is as follows: 1000 ml of anhydrous ethanol was added to *Acanthopanax senticosus* natural product (100 g) purchased from the Korea Plant Extract Bank (Daejeon, Korea), and the *Acanthopanax senticosus* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Acanthopanax senticosus*.

[Reference Example 6] Preparation of *Inulae radix* Extract

The preparation method of the *Inulae radix* extract of the present disclosure is as follows: 1000 ml of anhydrous ethanol was added to *Inulae radix* natural product (100 g) purchased from the Korea Plant Extract Bank (Daejeon, Korea), and the *Inulae radix* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer: Buchi, temperature: 40° C.), and then freeze-dried to obtain a dried extract of *Inulae radix*.

[Reference Example 7] Preparation of *Dioscorea japonica* Extract

The preparation method of the *Dioscorea japonica* extract of the present disclosure is as follows: 1000 ml of anhydrous ethanol was added to *Dioscorea japonica* natural product (100 g) purchased from the Korea Plant Extract Bank (Daejeon, Korea), and the *Dioscorea japonica* natural product was extracted using an extractor equipped with a reflux cooler (model: HB 4 basic, manufacturer: IKA) at 80° C. for 2 hours while heating. After filtering the extract with a Whatman No. 2 filter paper, the remaining residue was extracted one or more times in the same manner as above, and the obtained extracts were combined and concentrated under reduced pressure (model: Rotavapor, manufacturer:

Buchi, temperature: 40° C.), and then freeze-dried to obtain a dried extract of *Dioscorea japonica*.

[Test Example 1] Evaluation of Sebum Production Inhibitory Activity

In order to efficiently evaluate the sebum production inhibitory activity of the plant extracts of the present disclosure, sebaceous gland cells and keratinocytes were used together, and an environment in vitro model similar to that of human sebaceous glands of the hair was used. HaCaT (ATCC, Va., USA), keratinocytes (Cellprogen, Calif., USA) cells and human sebaceous gland cells were inoculated into a 24-well culture plate at $3.75 \times 10^4$ cells and $6.0 \times 10^4$ cells, respectively. After inoculation, it was allowed to stand for one day so that the cells adhered to the bottom of the culture plate. At this time, 10% of fetal bovine serum (JRH Bioscience, Tokyo, Japan), 100 mg/ml of penicillin, and 100 mg/ml of streptomycin (the above two reagents, GIBCO, Milan, Italy) were added to DMEM medium (Invitrogen, Carlsbad, Calif.) and used as a medium.

After one day, the cells were treated with 50 µM of linoleic acid, 50 µM of arachidonic acid, or 10 nM of dihydrotestosterone, as a stimulating source for causing seborrheic skin inflammation. At the same time, each plant extract obtained in Reference Examples 1 to 7 in the experimental group was dissolved in DMSO to make a 1% solution, and then diluted in DMEM medium, and treated to a final concentration of 50 ppm. After one day, the amount of triglycerides produced in the cells was measured using Oil Red O staining. In addition, for comparison, retinol, known to have sebum production inhibitory activity, was treated at a concentration of 0.3 ppm instead of the plant extracts.

In order to determine the sebum production inhibitory activity, more specifically, the following procedure was carried out: one day after the treatment with Reference Examples 1 to 7, or retinol, the cells washed with PBS were fixed with a 3.7% formaldehyde solution for 30 minutes. The fixed cells were washed three times with PBS and once with 70% ethanol, and then stained for 30 minutes with a 0.4% Oil Red 0 solution. The stained cells were washed once with 70% ethanol and three times with PBS. Then, the oil red 0 solution stained with isopropanol was dissolved again, and the absorbance was measured at 520 nm using a spectrophotometer for quantification.

The measurement results are shown in Table 1 below.

TABLE 1

| Ingredients | Inhibition rate of sebum production (%) |
| --- | --- |
| *Cimicifugae rhizoma* | 61.9 |
| *Solani nigri herba* | 93.1 |
| *Glycyrrhiza uralensis* | 66.8 |
| *Clematis mandshurica* | 98.8 |
| *Acanthopanax senticosus* | 81.6 |
| *Inulae radix* | 113.5 |
| *Dioscorea japonica* | 83.1 |
| Retinol | 42.1 |

As shown in Table 1, the extracts selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica*, which were materials used as an active ingredient in the compositions of the present disclosure, exhibited excellent sebum production inhibitory activity. In addition, in the case of retinol which is a known sebum production inhibitor, it is easily destroyed by external factors such as light, temperature, oxygen and the like, and causes skin irritation. Thus, its use in large amounts is restricted, despite of its excellent efficacy, and there is a limitation in obtaining a high level of sebum production inhibitory activity by the use of small amounts. Meanwhile, since the extracts selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica* that are used in the compositions of the present disclosure are natural materials safe for the skin, a higher sebum production inhibitory activity can be obtained by the use of sufficient amounts.

Further, the evaluation was performed in the same manner as described above, but the combinations of the two extracts selected from. Reference Examples 1 to 7 were treated to the cells by 25 ppm each, finally at a concentration of 50 ppm, and the measurement results are shown in Table 2 below.

TABLE 2

| Ingredients | Inhibition rate of sebum production (%) |
| --- | --- |
| *Cimicifugae rhizoma*, *Solani nigri herba* | 82.5 |
| *Cimicifugae rhizoma*, *Glycyrrhiza uralensis* | 75.1 |
| *Cimicifugae rhizoma*, *Clematis mandshurica* | 88.8 |
| *Cimicifugae rhizoma*, *Acanthopanax senticosus* | 65.5 |
| *Cimicifugae rhizoma*, *Inulae radix* | 82.5 |
| *Cimicifugae rhizoma*, *Dioscorea japonica* | 77.8 |
| *Solani nigri herba*, *Glycyrrhiza uralensis* | 75.8 |
| *Solani nigri herba*, *Clematis mandshurica* | 100.5 |
| *Solani nigri herba*, *Acanthopanax senticosus* | 90.5 |
| *Solani nigri herba*, *Inulae radix* | 108.8 |
| *Solani nigri herba*, *Dioscorea japonica* | 92.1 |
| *Glycyrrhiza uralensis*, *Clematis mandshurica* | 88.9 |
| *Glycyrrhiza uralensis*, *Acanthopanax senticosus* | 90.8 |
| *Glycyrrhiza uralensis*, *Inulae radix* | 88.8 |
| *Glycyrrhiza uralensis*, *Dioscorea japonica* | 77.2 |
| *Clematis mandshurica*, *Acanthopanax senticosus* | 87.8 |
| *Clematis mandshurica*, *Inulae radix* | 120.3 |
| *Clematis mandshurica*, *Dioscorea japonica* | 92.1 |
| *Acanthopanax senticosus*, *Inulae radix* | 101.4 |
| *Acanthopanax senticosus*, *Dioscorea japonica* | 78.7 |
| *Inulae radix*, *Dioscorea japonica* | 95.2 |

As shown in Table 2, it can be seen that the extracts of two or more selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica* exhibit excellent sebum production inhibitory activity, and the above activity is significantly higher level as compared with when one type of extract was treated.

[Test Example 2] Evaluation of Procollagen-I Production Activity

An enzyme-linked immunosorbent assay (ELISA) method was used to confirm the amount of procollagen-I produced by the plant extracts of the present disclosure (Youngren et al., 1999). Since procollagen-I is a substance secreted out of cells, the culture solution of the fibroblasts treated with the samples was collected and applied to the experiment as a measurement method for confirming the expression change using the cell culture solution.

Specifically, human fibroblasts (Cell biologics, IL, USA) were inoculated into a 24-well culture plate at $2.5 \times 10^4$ cells. After inoculation, it was allowed to stand for one day so that the cells adhered to the bottom of the culture plate. At this time, 2% of low serum growth supplement (LSGS; Thermo Fisher, Mass., USA), 100 mg/ml of penicillin, and 100 mg/ml of streptomycin (the above two reagents, GIBCO, Milan, Italy) were added to 106 medium (Thermo Fisher, Mass., USA) and used as a medium. Each plant extract obtained in Reference Examples 1 to 7 in the experimental group was dissolved in DMSO to make a 1% solution, and then diluted in DMEM medium, and treated to a final concentration of 50 ppm. In addition, for comparison, TGF-β1, known to have the ability to produce procollagen-I, was treated at a concentration of 0.005 ppm instead of the plant extracts. Two days after the treatment with the samples, the production of procollagen-I was measured.

In order to determine the degree of procollagen-I production, more specifically, the following procedure was performed: procollagen-I antibodies (Santa Cruz Biotechnology, USA) were diluted in carbonate/bicarbonate (15 mM $Na_2CO_3$, 35 mM $NaHCO_3$, pH 9.6) buffer in a ratio of 1:100, and then coated onto a 96-well immulon-1 flat-bottomed-plate, treated with 1% BSA and blocked at room temperature for 1 hour. After blocking, the cell culture solution was added to the plate and allowed to react at 4° C. for 18 hours. After the reaction, the cells were washed with PBS containing 0.05% Tween 20, and the procollagen-I antibodies were added thereto and allowed to react at room temperature for 1 hour, followed by washing with 100 μL of PBS. Then, the secondary antibodies (horse reddish peroxidase, HRP) corresponding to the procollagen-I antibodies were allowed to react at room temperature for 1 hour and washed with 100 μL of PBS. After the reaction using a TMB substrate solution (Pierce, USA), the absorbance was measured at a wavelength of 490 nm to confirm the degree of color development, thereby confirming the production amount of procollagen-I. The measurement results are shown in Table 3 below.

TABLE 3

| Ingredients | Production rate of Procollagen-I (%) |
|---|---|
| Cimicifugae rhizoma | 51.4 |
| Solani nigri herba | 49.3 |
| Glycyrrhiza uralensis | 47.0 |
| Clematis mandshurica | 35.6 |
| Acanthopanax senticosus | 31.7 |
| Inulae radix | 17.3 |
| Dioscorea japonica | 9.8 |
| TGF-β1 | 52.1 |

As shown in Table 3, it can be seen that the extracts of one or more selected from the group consisting of *Cimicifugae rhizoma, Solani nigri herba, Glycyrrhiza uralensis, Clematis mandshurica, Acanthopanax senticosus, Inulae radix* and *Dioscorea japonica*, which are materials used as an active ingredient in the compositions of the present disclosure, exhibit excellent procollagen production-promoting effect, and that some extracts exhibit a significant level of procollagen production-promoting effect as compared with when TGF-β1, which is a known procollagen-I-producing substance, was treated.

In addition, the evaluation was performed in the same manner as described above, but the combinations of two extracts selected from. Reference Examples 1 to 7 were treated to the cells by 25 ppm each, finally at a concentration of 50 ppm, and the measurement results are shown in Table 4 below.

TABLE 4

| Ingredients | Production rate of Procollagen-I (%) |
|---|---|
| Cimicifugae rhizoma, Solani nigri herba | 45 |
| Cimicifugae rhizoma, Glycyrrhiza uralensis | 55.2 |
| Cimicifugae rhizoma, Clematis mandshurica | 40.5 |
| Cimicifugae rhizoma, Acanthopanax senticosus | 32.2 |
| Cimicifugae rhizoma, Inulae radix | 60.2 |
| Cimicifugae rhizoma, Dioscorea japonica | 45.2 |
| Solani nigri herba, Glycyrrhiza uralensis | 60.8 |
| Solani nigri herba, Clematis mandshurica | 78.8 |
| Solani nigri herba, Acanthopanax senticosus | 60.2 |
| Solani nigri herba, Inulae radix | 42.5 |
| Solani nigri herba, Dioscorea japonica | 32.2 |
| Glycyrrhiza uralensis, Clematis mandshurica | 45.1 |
| Glycyrrhiza uralensis, Acanthopanax senticosus | 49.7 |
| Glycyrrhiza uralensis, Inulae radix | 35.6 |
| Glycyrrhiza uralensis, Dioscorea japonica | 21.6 |
| Clematis mandshurica, Acanthopanax senticosus | 55.2 |
| Clematis mandshurica, Inulae radix | 47.1 |
| Clematis mandshurica, Dioscorea japonica | 42.3 |
| Acanthopanax senticosus, Inulae radix | 31.2 |
| Acanthopanax senticosus, Dioscorea japonica | 17.6 |
| Inulae radix, Dioscorea japonica | 35.8 |

As shown in Table 4, it can be seen that the extracts of two or more selected from the group consisting of *Cimicifugae rhizoma, Solani nigri herba, Glycyrrhiza uralensis, Clematis mandshurica, Acanthopanax senticosus, Inulae radix* and *Dioscorea japonica* exhibited excellent procollagen production-promoting effect, and the above effect is significantly higher level as compared with when one type of extract was treated.

From the above results, it can be seen that the extracts of one or more selected from the group consisting of *Cimic-* ifugae rhizoma, Solani nigri herba, Glycyrrhiza uralensis, Clematis mandshurica, Acanthopanax senticosus, Inulae radix and Dioscorea japonica that are used in the present disclosure promote the synthesis of procollagen-I while showing sebum production inhibitory effect, and thus can effectively function in pore reduction.

[Reference Example 8] Preparation of Examples 1 to 28

Nutritive creams were prepared according to a conventional method using the composition shown in Table 5 below. At this time, the combinations of the extracts included therein are shown in Table 6, and the combinations contained the same amount of each extract.

TABLE 5

(Unit: wt %)

| Ingredients | Examples |
| --- | --- |
| Extracts selected from the group consisting of *Cimicifugae rhizoma*, *Solani nigri herba*, *Glycyrrhiza uralensis*, *Clematis mandshurica*, *Acanthopanax senticosus*, Inulae radix and *Dioscorea japonica* | 2 |
| Polysorbate 60 | 1.5 |
| Sorbitan sesquioleate | 0.5 |
| PEG-60 Hydrogenated castor oil | 2 |
| Liquid paraffin | 10 |
| Squalane | 5 |
| Caprine/capryl triglyceride | 5 |
| Glycerin | 5 |
| Butylene glycol | 3 |
| Propylene glycol | 3 |
| Triethanolamine | 0.2 |
| Preservatives, pigments, flavors | q.s. |
| Purified water | balance |

TABLE 6

| Examples | Ingredients |
| --- | --- |
| Example 1 | Reference Example 1(*Cimicifugae rhizoma*) |
| Example 2 | Reference Example 2(*Solani nigri herba*) |
| Example 3 | Reference Example 3(*Glycyrrhiza uralensis*) |
| Example 4 | Reference Example 4(*Clematis mandshurica*) |
| Example 5 | Reference Example 5(*Acanthopanax senticosus*) |
| Example 6 | Reference Example 6(Inulae radix) |
| Example 7 | Reference Example 7(*Dioscorea japonica*) |
| Example 8 | Reference Example 1(*Cimicifugae rhizoma*) + Reference Example 2(*Solani nigri herba*) |
| Example 9 | Reference Example 1(*Cimicifugae rhizoma*) + Reference Example 3(*Glycyrrhiza uralensis*) |
| Example 10 | Reference Example 1(*Cimicifugae rhizoma*) + Reference Example 4(*Clematis mandshurica*) |
| Example 11 | Reference Example 1(*Cimicifugae rhizoma*) + Reference Example 5(*Acanthopanax senticosus*) |
| Example 12 | Reference Example 1(*Cimicifugae rhizoma*) + Reference Example 6(Inulae radix) |
| Example 13 | Reference Example 1(*Cimicifugae rhizoma*) + Reference Example 7(*Dioscorea japonica*) |
| Example 14 | Reference Example 2(*Solani nigri herba*) + Reference Example 3(*Glycyrrhiza uralensis*) |
| Example 15 | Reference Example 2(*Solani nigri herba*) + Reference Example 4(*Clematis mandshurica*) |
| Example 16 | Reference Example 2(*Solani nigri herba*) + Reference Example 5(*Acanthopanax senticosus*) |
| Example 17 | Reference Example 2(*Solani nigri herba*) + Reference Example 6(Inulae radix) |
| Example 18 | Reference Example 2(*Solani nigri herba*) + Reference Example 7(*Dioscorea japonica*) |
| Example 19 | Reference Example 3(*Glycyrrhiza uralensis*) + Reference Example 4(*Clematis mandshurica*) |
| Example 20 | Reference Example 3(*Glycyrrhiza uralensis*) + Reference Example 5(*Acanthopanax senticosus*) |
| Example 21 | Reference Example 3(*Glycyrrhiza uralensis*) + Reference Example 6(Inulae radix) |
| Example 22 | Reference Example 3(*Glycyrrhiza uralensis*) + Reference Example 7(*Dioscorea japonica*) |
| Example 23 | Reference Example 4(*Clematis mandshurica*) + Reference Example 5(*Acanthopanax senticosus*) |
| Example 24 | Reference Example 5(*Clematis mandshurica*) + Reference Example 6(Inulae radix) |
| Example 25 | Reference Example 4(*Clematis mandshurica*) + Reference Example 7(*Dioscorea japonica*) |
| Example 26 | Reference Example 5(*Acanthopanax senticosus*) + Reference Example 6(Inulae radix) |
| Example 27 | Reference Example 5(*Acanthopanax senticosus*) + Reference Example 1(*Dioscorea japonica*) |
| Example 28 | Reference Example 6(Inulae radix) + Reference Example 7(*Dioscorea japonica* |

[Test Example 3] Evaluation of Human Pores 280 men and women having large amounts of sebum secretion on their faces and large facial pores were selected and randomly divided into 28 groups of 10 people. They were allowed to apply the nutritional creams prepared according to the prescriptions of Tables 5 and 6 to the areas with large sebum secretion and large pores, mainly around the skins of the cheeks and nose, for 4 weeks after washing every evening. Measurement was carried out by visual evaluation and device measurement before and after using the test products under constant temperature and humidity conditions. The visual evaluation was scored according to the degree of feeling experienced by the person participating in the test and is shown in Table 7, and the skin pore size was measured using a pore size measuring device (Skin touch, developed by Amorepacific) and the results are shown in Table 8 below. In addition, the amount of sebum was measured using a sebumeter and the results are shown in Table 9 below.

TABLE 7

| Ingredients | Pore Evaluation Score |
| --- | --- |
| Example 1 | 1.37 |
| Example 2 | 1.92 |
| Example 3 | 1.55 |
| Example 4 | 1.63 |
| Example 5 | 1.25 |
| Example 6 | 1.61 |
| Example 7 | 0.98 |
| Example 8 | 1.58 |
| Example 9 | 1.63 |
| Example 10 | 1.63 |
| Example 11 | 1.28 |
| Example 12 | 1.88 |
| Example 13 | 1.75 |
| Example 14 | 1.82 |
| Example 15 | 2.15 |
| Example 16 | 1.92 |
| Example 17 | 1.88 |
| Example 18 | 1.72 |
| Example 19 | 1.68 |
| Example 20 | 1.92 |
| Example 21 | 1.63 |
| Example 22 | 1.51 |
| Example 23 | 1.88 |
| Example 24 | 1.88 |
| Example 25 | 1.66 |
| Example 26 | 1.68 |

TABLE 7-continued

| Ingredients | Pore Evaluation Score |
| --- | --- |
| Example 27 | 1.22 |
| Example 28 | 1.78 |

<Criteria for Determining Effects>

0: Almost no effect, 1: Little effect, 2: Significantly improved, 3: Completely satisfied

TABLE 8

| Ingredients | Pore size before use (pixel) | Pore size after use (pixel) |
| --- | --- | --- |
| Example 1 | 208 | 197 |
| Example 2 | 206 | 192 |
| Example 3 | 207 | 198 |
| Example 4 | 207 | 188 |
| Example 5 | 208 | 201 |
| Example 6 | 206 | 193 |
| Example 7 | 208 | 199 |
| Example 8 | 210 | 192 |
| Example 9 | 208 | 193 |
| Example 10 | 209 | 194 |
| Example 11 | 207 | 199 |
| Example 12 | 206 | 188 |
| Example 13 | 208 | 192 |
| Example 14 | 209 | 193 |
| Example 15 | 211 | 189 |
| Example 16 | 208 | 191 |
| Example 17 | 206 | 190 |
| Example 18 | 205 | 193 |
| Example 19 | 208 | 196 |
| Example 20 | 206 | 191 |
| Example 21 | 204 | 195 |
| Example 22 | 206 | 199 |
| Example 23 | 202 | 187 |
| Example 24 | 208 | 185 |
| Example 25 | 209 | 195 |
| Example 26 | 208 | 199 |
| Example 27 | 206 | 201 |
| Example 28 | 205 | 199 |

TABLE 9

| Ingredients | Sebum amount before use ($\mu g/cm^2$ h) | Sebum amount after use ($\mu g/cm^2$ h) |
| --- | --- | --- |
| Example 1 | 71.5 | 65.8 |
| Example 2 | 70.8 | 59.1 |
| Example 3 | 72.8 | 65.1 |
| Example 4 | 73.6 | 62.1 |
| Example 5 | 72.1 | 61.3 |
| Example 6 | 71.1 | 59.8 |
| Example 7 | 73.2 | 65.2 |
| Example 8 | 72.1 | 60.1 |
| Example 9 | 71.5 | 59.8 |
| Example 10 | 70.8 | 57.2 |
| Example 11 | 70.8 | 65.2 |
| Example 12 | 72.1 | 57.2 |
| Example 13 | 71.6 | 61.2 |
| Example 14 | 72.4 | 62.3 |
| Example 15 | 71.4 | 55.8 |
| Example 16 | 71.9 | 58.1 |
| Example 17 | 72.5 | 59.3 |
| Example 18 | 70.5 | 60.2 |
| Example 19 | 73.8 | 63.8 |
| Example 20 | 71.5 | 58.4 |
| Example 21 | 69.5 | 62.2 |
| Example 22 | 73.1 | 66.9 |
| Example 23 | 76.2 | 56.3 |
| Example 24 | 72.1 | 53.9 |
| Example 25 | 75.8 | 61.2 |
| Example 26 | 74.8 | 61.7 |

TABLE 9-continued

| Ingredients | Sebum amount before use ($\mu g/cm^2$ h) | Sebum amount after use ($\mu g/cm^2$ h) |
| --- | --- | --- |
| Example 27 | 74.1 | 65.3 |
| Example 28 | 72.9 | 63.1 |

As shown in Tables 7 to 9, when the compositions containing the extracts of one or more selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica*, as an active ingredient, were used, it can be confirmed that, in fact, the pore size is reduced and the amount of sebum secretion is reduced as compared with before use, and that the users also have a feeling that the compositions are effective.

[Preparation Example 1] Cosmetic Lotion

A cosmetic lotion was prepared according to a conventional method using the composition shown in Table 10 below.

TABLE 10

| | Content (wt %) |
| --- | --- |
| Extracts of one or more selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica* | 1.0 |
| Glycerin | 3.0 |
| Butylene glycol | 2.0 |
| Propylene glycol | 2.0 |
| Carboxyvinyl polymer | 0.1 |
| PEG-12 Nonylphenyl ether | 0.2 |
| Polysorbate 80 | 0.4 |
| Ethanol | 10.0 |
| Triethanolamine | 0.1 |
| Preservatives, pigments, flavors | q.s. |
| Purified water | balance |

[Preparation Example 2] Massage Cream

A massage cream was prepared according to a conventional method using the composition shown in Table 11 below.

TABLE 11

| | Content (wt %) |
| --- | --- |
| Extracts of one or more selected from the group consisting of *Cimicifugae rhizoma*, *Solani nigri herba*, *Glycyrrhiza uralensis*, *Clematis mandshurica*, *Acanthopanax senticosus*, *Inulae radix* and *Dioscorea japonica* | 1.0 |
| Beewax | 10.0 |
| Polysorbate 60 | 1.5 |
| PEG-60 Hydrogenated castor oil | 2.0 |
| Sorbitan sesquioleate | 0.8 |
| Liquid paraffin | 40.0 |
| Squalane | 5.0 |
| Caprine/capryl triglyceride | 4.0 |
| Glycerin | 5.0 |
| Butylene glycol | 3.0 |

TABLE 11-continued

| | Content (wt %) |
|---|---|
| Propylene glycol | 3.0 |
| Triethanolamine | 0.2 |
| Preservatives, pigments, flavors | q.s. |
| Purified water | balance |

[Preparation Example 3] Pack

A pack was prepared according to a conventional method using the composition shown in Table 12 below.

TABLE 12

| | Content (wt %) |
|---|---|
| Extracts of one or more selected from the group consisting of *Cimicifugae rhizoma*, *Solani nigri herba*, *Glycyrrhiza uralensis*, *Clematis mandshurica*, *Acanthopanax senticosus*, Inulae radix and *Dioscorea japonica* | 1.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG-12 Nonylphenyl ether | 0.3 |
| Polysorbate 60 | 0.3 |
| Preservatives, pigments, flavors | q.s. |
| Purified water | balance |

[Preparation Example 4] Gel

A gel was prepared according to a conventional method using the composition shown in Table 13 below.

TABLE 13

| | Content (wt %) |
|---|---|
| Extracts of one or more selected from the group consisting of *Cimicifugae rhizoma*, *Solani nigri herba*, *Glycyrrhiza uralensis*, *Clematis mandshurica*, *Acanthopanax senticosus*, Inulae radix and *Dioscorea japonica* | 1.0 |
| Ethylenediamine sodium acetate | 0.05 |
| Glycerin | 5.0 |
| Carboxyvinyl polymer | 0.3 |
| Ethanol | 5.0 |
| PEG-60 Hydrogenated castor oil | 0.5 |
| Triethanolamine | 0.3 |

TABLE 13-continued

| | Content (wt %) |
|---|---|
| Preservatives, pigments, flavors | q.s. |
| Purified water | balance |

[Preparation Example 5] Ointment

An ointment was prepared according to a conventional method using the composition shown in Table 14 below.

TABLE 14

| | Content (wt %) |
|---|---|
| Extracts of one or more selected from the group consisting of *Cimicifugae rhizoma*, *Solani nigri herba*, *Glycyrrhiza uralensis*, *Clematis mandshurica*, *Acanthopanax senticosus*, Inulae radix and *Dioscorea japonica* | 1.0 |
| Glycerin | 8.0 |
| Butylene glycol | 4.0 |
| Liquid paraffin | 15.0 |
| Beta glucan | 7.0 |
| Carbomer | 0.1 |
| Caprylic/capric triglycerides | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservatives, pigments, flavors | q.s. |
| Purified water | Residual amount |

Although specific parts of the present disclosure have been described in detail, it will be apparent to those skilled in the art that these specific descriptions are merely a preferred embodiment and that the scope of the present disclosure is not limited thereto. Therefore, the substantial scope of the present disclosure will be defined by the accompanying claims and their equivalents.

The invention claimed is:

1. A method for controlling sebum secretion and/or reducing pore size of skin of a subject, comprising topically applying a cosmetic composition comprising, a combination of same amount of extract *Solani nigri herba* and extract of *Clematis mandshurica* to the skin of the subject.

2. The method of claim 1, wherein the combination of the extracts of *Solani nigri herba* and *Clematis mandshurica* are contained in an amount of 0.001 to 10% by weight relative to the total weight of the composition.

3. The method of claim 1, wherein the combination of the extracts of *Solani nigri herba* and *Clematis mandshurica* are prepared using ethanol or heated water as an extraction solvent.

* * * * *